US008512408B2

(12) United States Patent
Miller et al.

(10) Patent No.: US 8,512,408 B2
(45) Date of Patent: Aug. 20, 2013

(54) FLEXIABLE SPINAL IMPLANT

(75) Inventors: Keith Miller, Germantown, TN (US); Richard A. Hynes, Melborne Beach, FL (US); Kidong Yu, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 286 days.

(21) Appl. No.: 12/971,861

(22) Filed: Dec. 17, 2010

(65) Prior Publication Data
US 2012/0158140 A1   Jun. 21, 2012

(51) Int. Cl.
*A61F 2/44* (2006.01)
(52) U.S. Cl.
USPC ........................................ 623/17.16
(58) Field of Classification Search
USPC ............................. 623/17.11–17.16
See application file for complete search history.

(56) References Cited

U.S. PATENT DOCUMENTS

| | | |
|---|---|---|
| 5,171,278 A | 12/1992 | Pisharodi |
| 5,320,644 A | 6/1994 | Baumgartner |
| 5,390,683 A | 2/1995 | Pisharodi |
| 5,749,916 A | 5/1998 | Richelsoph |
| 5,755,797 A | 5/1998 | Baumgartner |
| 5,782,832 A | 7/1998 | Larsen et al. |
| 5,860,973 A | 1/1999 | Michelson |
| 5,919,235 A | 7/1999 | Husson et al. |
| 6,039,761 A | 3/2000 | Li et al. |
| 6,080,158 A | 6/2000 | Lin |
| 6,126,689 A | 10/2000 | Brett |
| 6,190,414 B1 | 2/2001 | Young et al. |
| 6,193,757 B1 | 2/2001 | Foley et al. |
| 6,206,923 B1 | 3/2001 | Boyd et al. |
| 6,251,140 B1 | 6/2001 | Marino et al. |
| 6,368,351 B1 | 4/2002 | Glenn et al. |
| 6,387,130 B1 | 5/2002 | Stone et al. |
| 6,395,031 B1 | 5/2002 | Foley et al. |
| 6,409,766 B1 | 6/2002 | Brett |
| 6,488,710 B2 | 12/2002 | Besselink |
| 6,610,094 B2 | 8/2003 | Husson |
| 6,613,089 B1 | 9/2003 | Estes et al. |
| 6,620,196 B1 | 9/2003 | Trieu |
| 6,656,178 B1 | 12/2003 | Veldhuizen et al. |
| 6,660,037 B1 | 12/2003 | Husson et al. |
| 6,685,742 B1 | 2/2004 | Jackson |
| 6,723,126 B1 | 4/2004 | Berry |
| 6,743,257 B2 | 6/2004 | Castro |
| 6,833,006 B2 | 12/2004 | Foley et al. |
| 6,913,621 B2 | 7/2005 | Boyd et al. |
| 6,953,477 B2 | 10/2005 | Berry |

(Continued)

FOREIGN PATENT DOCUMENTS

| | | |
|---|---|---|
| EP | 1925271 A1 | 5/2008 |
| WO | 2008016597 A2 | 2/2008 |
| WO | 2008152501 A2 | 12/2008 |

*Primary Examiner* — Ellen C Hammond

(57) ABSTRACT

A spinal implant for positioning in a space formed between vertebral members. The implant includes a number of sections that are pivotally attached together at pivot axes. The pivot axes include connectors that extend through at least a portion of the sections and are configured for the sections to be pivotally attached for the implant to be flexible to facilitate insertion into the space and to be configurable to the space. One of the sections may include a receptacle that is contained within the section. The receptacle has a fixed size and shape that holds bone growth material. The fixed size and shape of the receptacle prevents the bone growth from escaping during flexing of the implant.

20 Claims, 14 Drawing Sheets

(56) References Cited

U.S. PATENT DOCUMENTS

| | | |
|---|---|---|
| 7,018,413 B2 | 3/2006 | Kruger |
| 7,044,971 B2 | 5/2006 | Suddaby |
| 7,070,598 B2 | 7/2006 | Lim et al. |
| 7,083,649 B2 | 8/2006 | Zucherman et al. |
| 7,087,055 B2 | 8/2006 | Lim et al. |
| 7,097,648 B1 | 8/2006 | Globerman et al. |
| 7,214,243 B2 | 5/2007 | Taylor |
| 7,232,463 B2 | 6/2007 | Falahee |
| 7,318,839 B2 | 1/2008 | Malberg et al. |
| 7,326,216 B2 | 2/2008 | Bertagnoli |
| 7,351,262 B2 | 4/2008 | Bindseil et al. |
| 7,465,317 B2 | 12/2008 | Malberg et al. |
| 7,503,935 B2 | 3/2009 | Zucherman et al. |
| 7,503,936 B2 | 3/2009 | Trieu |
| 7,513,900 B2 | 4/2009 | Carrison et al. |
| 7,520,900 B2 | 4/2009 | Trieu |
| 7,578,849 B2 | 8/2009 | Trieu |
| 7,585,313 B2 | 9/2009 | Kwak et al. |
| 7,618,461 B2 | 11/2009 | Trieu |
| 7,625,377 B2 | 12/2009 | Veldhuizen et al. |
| 7,641,690 B2 | 1/2010 | Abdou |
| 7,655,042 B2 | 2/2010 | Foley et al. |
| 7,666,226 B2 | 2/2010 | Schaller |
| 7,666,227 B2 | 2/2010 | Schaller |
| 7,670,374 B2 | 3/2010 | Schaller |
| 7,670,375 B2 | 3/2010 | Schaller |
| 7,682,400 B2 | 3/2010 | Zwirkoski |
| 7,708,779 B2 | 5/2010 | Edie et al. |
| 7,731,751 B2 | 6/2010 | Butler et al. |
| 7,785,368 B2 | 8/2010 | Schaller |
| 7,799,056 B2 | 9/2010 | Sankaran |
| 8,343,224 B2 * | 1/2013 | Lynn et al. .................. 623/17.16 |
| 2001/0010021 A1 | 7/2001 | Boyd et al. |
| 2002/0026244 A1 | 2/2002 | Trieu |
| 2004/0167625 A1 | 8/2004 | Beyar et al. |
| 2004/0254643 A1 | 12/2004 | Jackson |
| 2005/0119747 A1 | 6/2005 | Fabris Monterumici et al. |
| 2005/0131540 A1 | 6/2005 | Trieu |
| 2005/0131541 A1 | 6/2005 | Trieu |
| 2005/0143827 A1 | 6/2005 | Globerman et al. |
| 2005/0154462 A1 | 7/2005 | Zucherman et al. |
| 2005/0154463 A1 | 7/2005 | Trieu |
| 2005/0278036 A1 | 12/2005 | Leonard et al. |
| 2006/0041258 A1 | 2/2006 | Galea |
| 2006/0089719 A1 | 4/2006 | Trieu |
| 2006/0136064 A1 | 6/2006 | Sherman |
| 2006/0142858 A1 | 6/2006 | Colleran et al. |
| 2006/0189999 A1 | 8/2006 | Zwirkoski |
| 2006/0235388 A1 | 10/2006 | Justis et al. |
| 2006/0241761 A1 | 10/2006 | Gately |
| 2006/0247778 A1 | 11/2006 | Ferree et al. |
| 2006/0247781 A1 | 11/2006 | Francis |
| 2006/0265077 A1 | 11/2006 | Zwirkoski |
| 2007/0005088 A1 | 1/2007 | LeHuec et al. |
| 2007/0016301 A1 | 1/2007 | Martinez et al. |
| 2007/0067034 A1 | 3/2007 | Chirico et al. |
| 2007/0067035 A1 | 3/2007 | Falahee |
| 2007/0073398 A1 | 3/2007 | Fabian et al. |
| 2007/0123986 A1 | 5/2007 | Schaller |
| 2007/0162132 A1 | 7/2007 | Messerli |
| 2007/0198025 A1 | 8/2007 | Trieu et al. |
| 2007/0225808 A1 | 9/2007 | Warnick |
| 2007/0233076 A1 | 10/2007 | Trieu |
| 2007/0260314 A1 | 11/2007 | Biyani |
| 2007/0282443 A1 | 12/2007 | Globerman et al. |
| 2007/0299521 A1 | 12/2007 | Glenn et al. |
| 2008/0009944 A1 | 1/2008 | McGuckin, Jr. |
| 2008/0058933 A1 | 3/2008 | Garner et al. |
| 2008/0125865 A1 | 5/2008 | Abdelgany |
| 2008/0133012 A1 | 6/2008 | McGuckin |
| 2008/0208344 A1 | 8/2008 | Kilpela et al. |
| 2008/0221687 A1 | 9/2008 | Viker |
| 2008/0234687 A1 | 9/2008 | Schaller et al. |
| 2008/0234827 A1 | 9/2008 | Schaller et al. |
| 2008/0243255 A1 | 10/2008 | Butler et al. |
| 2008/0249628 A1 * | 10/2008 | Altarac et al. .............. 623/17.16 |
| 2008/0281346 A1 | 11/2008 | Greenhalgh et al. |
| 2008/0312743 A1 | 12/2008 | Vila et al. |
| 2009/0005871 A1 | 1/2009 | White et al. |
| 2009/0012616 A1 | 1/2009 | James et al. |
| 2009/0012617 A1 | 1/2009 | White et al. |
| 2009/0012621 A1 | 1/2009 | James et al. |
| 2009/0012622 A1 | 1/2009 | James et al. |
| 2009/0012623 A1 | 1/2009 | Sack et al. |
| 2009/0030423 A1 | 1/2009 | Puno |
| 2009/0048676 A1 | 2/2009 | Fabian, Jr. |
| 2009/0054991 A1 | 2/2009 | Biyani et al. |
| 2009/0076607 A1 | 3/2009 | Aalsma et al. |
| 2009/0112318 A1 | 4/2009 | Butler et al. |
| 2009/0143859 A1 | 6/2009 | McClellan, III et al. |
| 2009/0182431 A1 | 7/2009 | Butler et al. |
| 2009/0204220 A1 | 8/2009 | Trieu |
| 2009/0234398 A1 | 9/2009 | Chirico et al. |
| 2009/0234454 A1 | 9/2009 | Siegal |
| 2009/0240335 A1 | 9/2009 | Arcenio et al. |
| 2009/0248092 A1 | 10/2009 | Bellas et al. |
| 2009/0292315 A1 | 11/2009 | Trieu |
| 2010/0106250 A1 | 4/2010 | Abdou |
| 2010/0121453 A1 | 5/2010 | Peterman |
| 2010/0161062 A1 | 6/2010 | Foley et al. |
| 2010/0168862 A1 | 7/2010 | Edie et al. |
| 2010/0174288 A1 | 7/2010 | Schaller |
| 2010/0174289 A1 | 7/2010 | Schaller |
| 2010/0174375 A1 | 7/2010 | Schaller |
| 2010/0191287 A1 | 7/2010 | Bucci |
| 2010/0191337 A1 | 7/2010 | Zamani et al. |
| 2010/0198263 A1 | 8/2010 | Siegal et al. |
| 2010/0256768 A1 | 10/2010 | Lim et al. |
| 2011/0029083 A1 | 2/2011 | Hynes et al. |
| 2011/0029085 A1 | 2/2011 | Hynes et al. |
| 2011/0125266 A1 * | 5/2011 | Rodgers et al. ............ 623/17.11 |

* cited by examiner

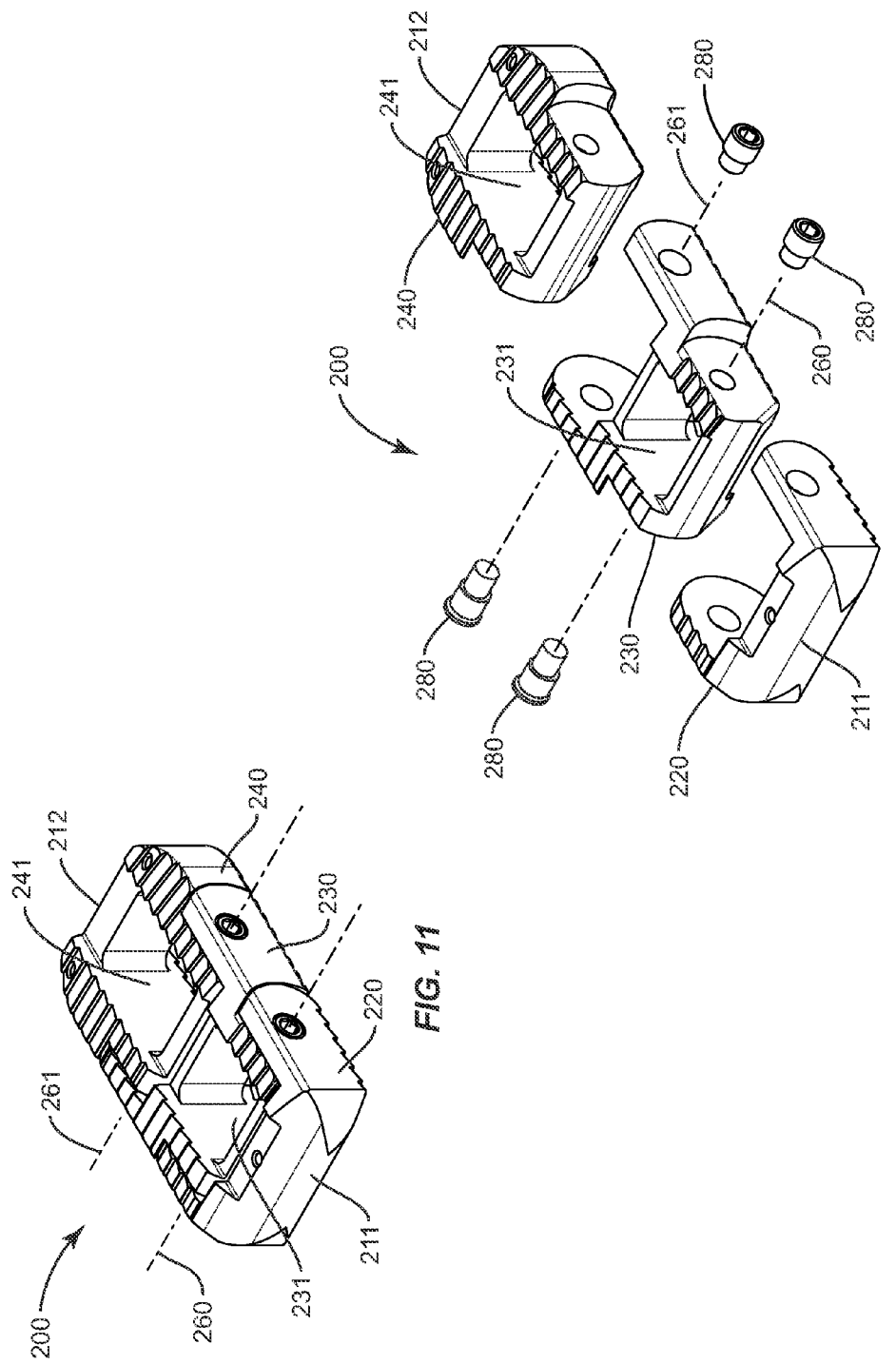

FLEXIABLE SPINAL IMPLANT

BACKGROUND

The present application is directed to implants for insertion between vertebral members and, more particularly, to implants with two or more sections that are pivotally attached together.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs and/or the vertebral members. The damage may result from a variety of causes including but not limited to a specific event such as trauma, a degenerative condition, a tumor, or infection. Damage to the intervertebral discs and vertebral members can lead to pain, neurological deficit, and/or loss of motion.

Various procedures include replacing the entirety or a section of a vertebral member, the entirety or a section of an intervertebral disc, or both. One or more replacement implants may be inserted to replace the damaged vertebral members and/or discs. The implants are configured to be inserted into the intervertebral space and contact against the remaining adjacent vertebral members. The implants reduce or eliminate the pain and neurological deficit, and increase the range of motion.

The implants should include an adjustable shape to facilitate insertion into the patient and placement between the vertebral members. Further, the curvature of the spine and general shapes of the vertebral members may make it difficult for the implants to adequately contact the adjacent vertebral members. There is a need for implants configurable to match the spinal anatomy for secure contact when implanted into an intervertebral space.

SUMMARY

The present application is directed to flexible spinal implants. The spinal implant may include a number of sections that each have a distal end and a proximal end, and a superior and inferior sides. One of the sections may include a receptacle bounded within an interior of the section and have a fixed size and shape. The receptacle may be open on the superior and inferior sides. Hinges may pivotally join together the sections in an end-to-end and articulating arrangement. Each of the hinges may connect together two of the sections. The hinges may be aligned along a plane. The receptacle may be aligned transverse to and extend across the plane. The receptacle may be open in both directions that face away from the plane.

The implant may also include sections that are pivotally attached together and aligned in an end-to-end orientation with each having a superior side and an inferior side. A first one of the sections may include a receptacle contained within an interior of the section and have distal, proximal, and lateral side walls. The receptacle may be open on the superior and inferior sides. The first section and a second section may be pivotally connected at a pivot axis that extends across the receptacle. The pivot axis may include a first connector that extends through first portions of the first and second sections and a second connector that extends through second portions of the first and second sections. The first and second connectors may be spaced apart along the pivot axis by a gap that is located in the receptacle.

The implant may also include first and second sections each having a distal end and a proximal end, lateral sides that extend between the ends, and a superior side and an inferior side. A receptacle may be contained within an interior of the first section and have a fixed size and shape. The receptacle may have a continuous side wall and may be open on the superior and inferior sides. A hinge may extend through the lateral sides of each of the first and second sections between the distal and proximal ends of each section. The hinge may pivotally connect the first and second sections along a pivot axis. The hinge may position the sections together in an end-to-end configuration with a longitudinal axis extending through the distal and proximal ends of each of the sections and between the superior and inferior sides and between the lateral sides. The pivot axis may extend across the receptacle and across the longitudinal axis.

The various aspects of the various embodiments may be used alone or in any combination, as is desired.

BRIEF DESCRIPTION OF THE DRAWINGS

FIG. 11 is a perspective view of a flexible spinal implant in a straight orientation.

FIG. 12 is an exploded view of the flexible spinal implant illustrated in FIG. 11.

DETAILED DESCRIPTION

Figure 1:
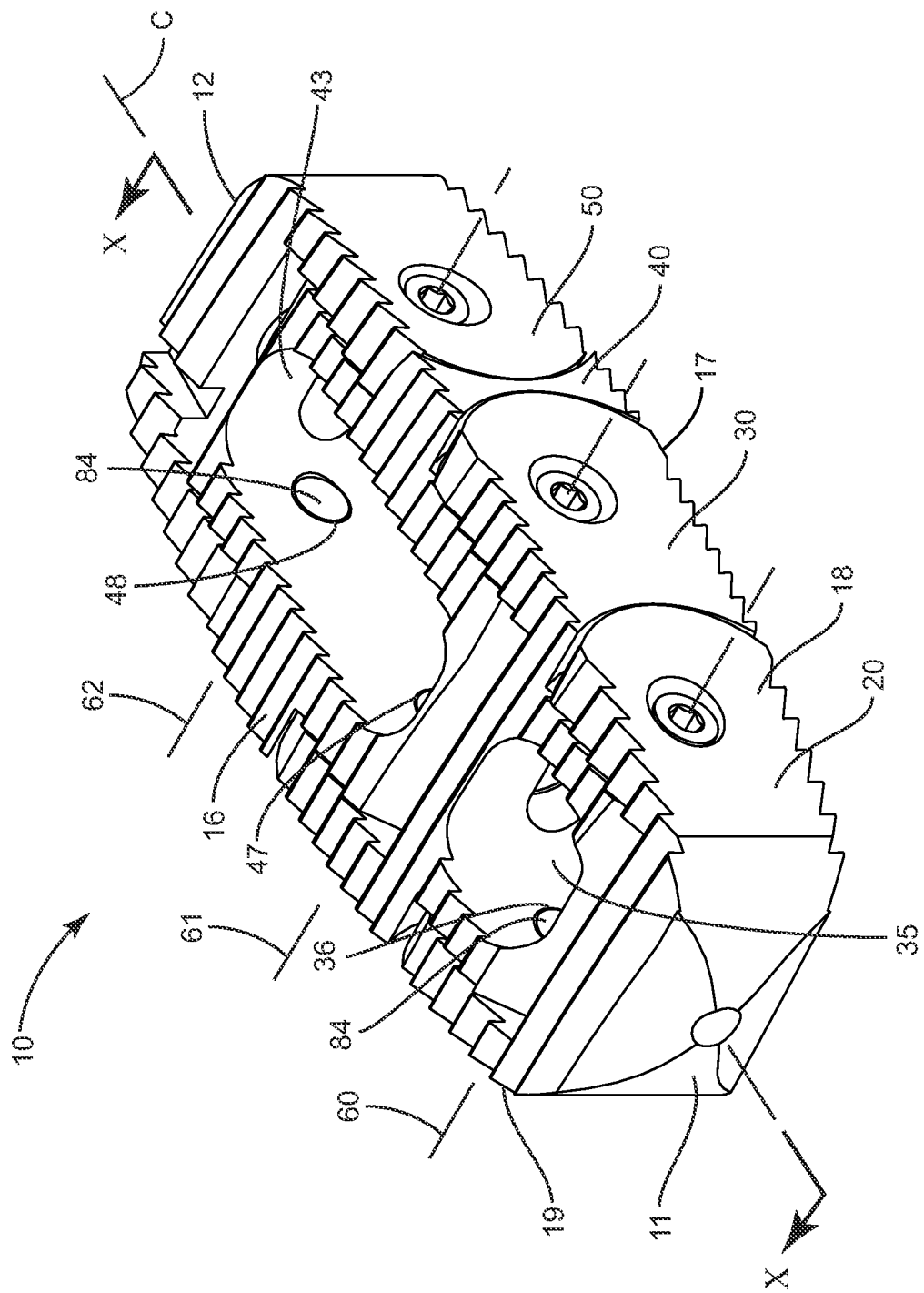
FIG. 1 is a perspective view of a flexible spinal implant in a straight orientation.

The present application is directed to flexible spinal implants. The implants include two or more separate sections that are pivotally attached together at pivot axes. The pivot axes give the implant flexibility for positioning at various orientations. The flexibility may facilitate insertion of the implant between the vertebral members, and may also allow the implant to conform to the shape of the intervertebral space.

FIGS. 1-10 illustrate a flexible implant 10 with an elongated shape formed by sections 20, 30, 40, 50. The implant 10 includes a distal end 11 that is initially inserted into the space between the vertebral members and an opposing proximal end 12. The elongated shape gives the implant 10 a longitudinal centerline C that extends through the ends 11, 12, and through the sections 20, 30, 40, 50. The implant 10 further includes lateral sides 18, 19 that extend along the longitudinal centerline C. The lateral sides 18, 19 of the implant 10 may include a convex curvature. In one embodiment, the curvature has a radius of about 106 mm. The implant 10 also includes a superior side 16 and an inferior side 17. The sides 16, 17 may include teeth that engage with the vertebral members.

The sections 20, 30, 40, 50 are attached together at pivot axes 60, 61, 62. Specifically, sections 20 and 30 are attached together at pivot axis 60, sections 30 and 40 are attached together at pivot axis 61, and sections 40 and 50 are attached together at pivot axis 62. The pivot axes 60, 61, 62 extend across the centerline C. In one embodiment, the pivot axes 60, 61, 62 are perpendicular to the centerline C.

Figure 4:
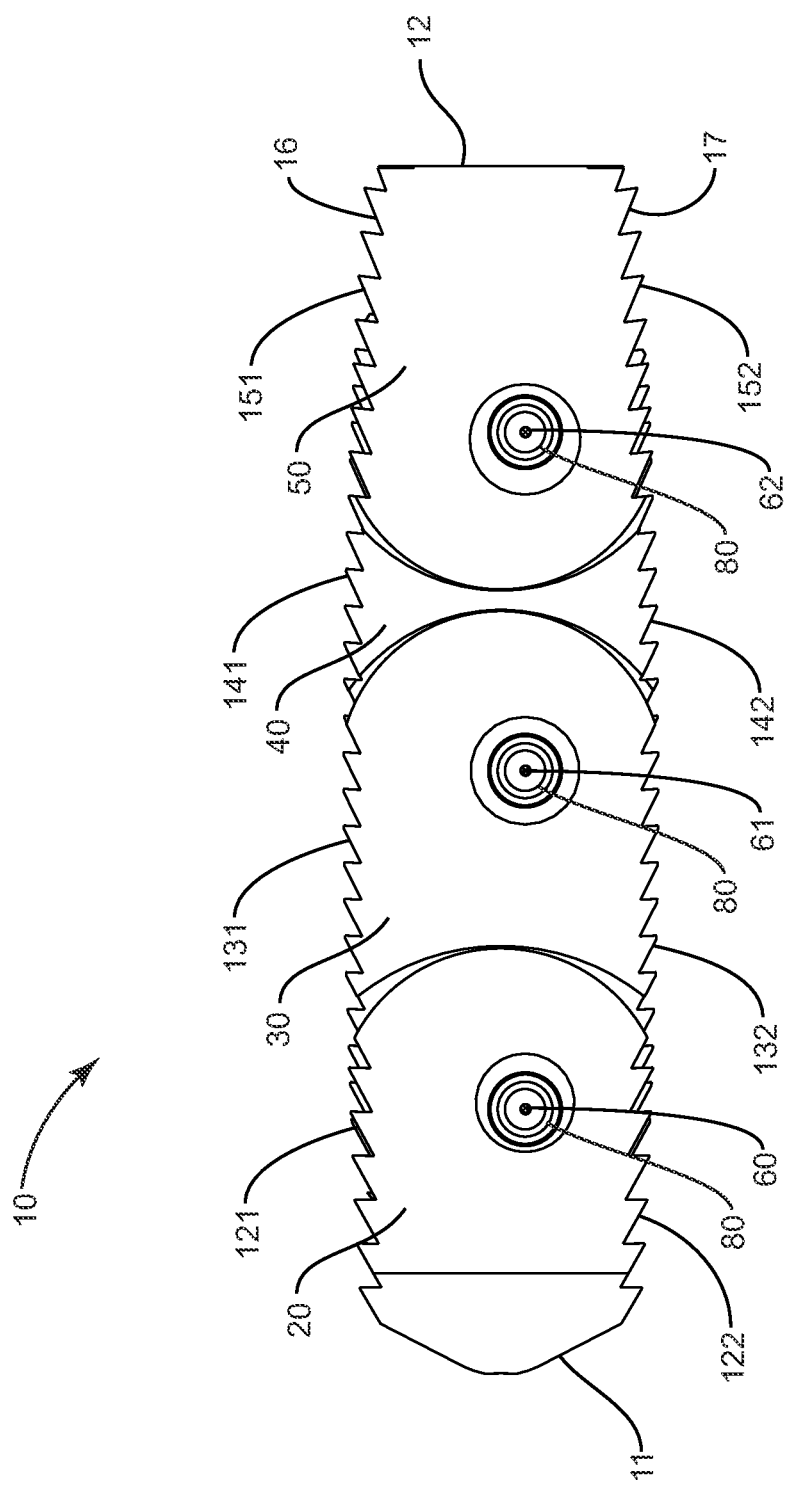
FIG. 4 is a side view of the flexible spinal implant illustrated in FIG. 1.

FIGS. 1 and 4 illustrate the implant 10 in a straight orientation. The sections 20, 30, 40, 50 are aligned to give the implant 10 a generally planar shape. The shapes of the sections 20, 30, 40, 50 may complement each other with superior surfaces 121, 131, 141, 151 and inferior surfaces 122, 132, 142, 152 of the sections being generally aligned.

Figure 3:
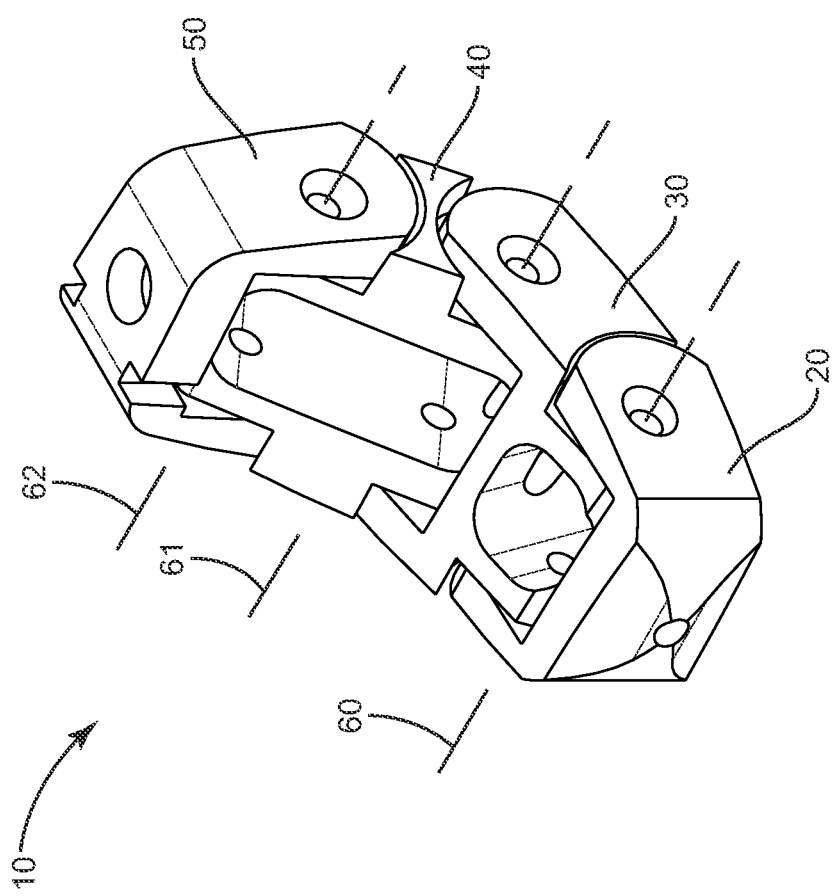
FIG. 3 is perspective view of the flexible spinal implant of FIG. 1 in a pivoted orientation.

The implant 10 may be moved to a variety of different pivoted orientations. These orientations include one or more of the sections 20, 30, 40, 50 pivoted away from the straight orientation. FIG. 3 includes the implant 10 in one pivoted orientation with each of the sections 20, 30, 40, 50 pivoted about their respective pivot axes 60, 61, 62. FIG. 3 specifically includes the implant 10 in a pivoted orientation with the sections 20, pivoted a lesser amount about pivot axis 60 than the amount sections 30 and 40 are pivoted about pivot axis 61, and the amount sections 40 and 50 are pivoted about pivot axis 62. The amount of pivoting between the respective sections 20, 30, 40, 50 may be adjusted accordingly to insert the implant 10 into the intervertebral space, and to accommodate the shape of the space.

Figure 2:
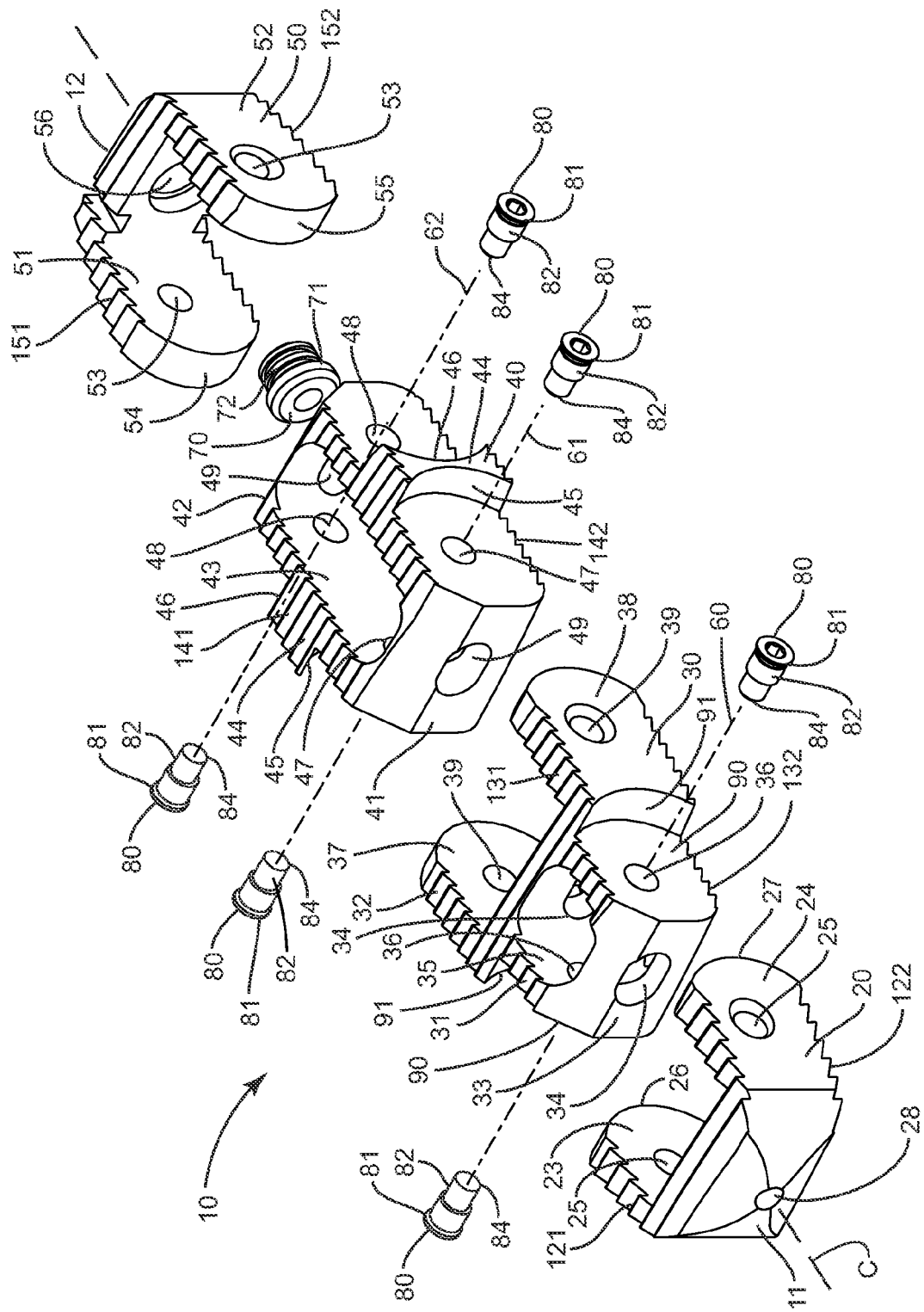
FIG. 2 is an exploded view of the flexible spinal implant illustrated in FIG. 1.

FIG. 2 illustrates an exploded view of the implant 10. Each of the sections 20, 30, 40, 50 is shaped and sized to be pivotally connected to the adjacent section. Section 20 is positioned at the distal section of the implant 10 and includes the distal end 11. The distal end 11 may include a tapered shape that facilitates insertion into the space between the vertebral members. The section 20 includes a pair of spaced-apart arms 23, 24 that extend in a proximal direction. The arms 23, 24 include curved proximal ends 26, 27 that facilitate pivoting movement with the section 30. The inner surfaces of the arms 23, 24 that face towards the longitudinal centerline C may be substantially smooth to further facilitate pivoting movement with the section 30. Apertures 25 extend through each of the arms 23, 24 to form a portion of the axis 60. Section 20 also includes a first surface 121 and an opposing second surface 122. Teeth may be positioned on one or both surfaces 121, 122 to maintain the position of the implant 10 in the intervertebral space.

Section 30 is positioned on a proximal side and adjacent to the section 20. Section 30 includes a first surface 131 and an opposing second surface 132. The surfaces 131, 132 may include teeth. Section 30 is further divided axially along the longitudinal centerline C into first and second portions 31, 32. The first portion 31 includes a width measured perpendicular to the centerline C to fit between the spaced apart arms 23, 24. The first portion 31 includes a face 33 positioned towards the section 20. The face 33 may be flat, or may have a curved shape. The first portion 31 also includes opposing lateral sides 90 that face outward away form the longitudinal centerline C.

The sides 90 may be substantially smooth and contact against the inner surfaces of the arms 23, 24. Apertures 36 extend through each of the sides 90 and form a portion of the axis 90.

A receptacle 35 extends through the section 30 from the first surface 131 to the second surface 132. The receptacle 35 is completely contained within the section 30 and includes a fixed shape. The receptacle 35 is configured to hold bone growth material to facilitate fusion with the vertebral members. The fixed shape causes the bone growth material to remain in the receptacle 35 during flexing of the implant 10. The apertures 36 that form a portion of the axis 60 may extend into the receptacle 35. Apertures 34 that extend along the longitudinal centerline C may also extend into the receptacle 35.

The second portion 32 includes a greater width measured perpendicular to the longitudinal centerline C than the first portion 31. Walls 91 face in a distal direction and are exposed laterally beyond the sides 90 of the first portion 31. The walls 91 include a curved shape that substantially matches the curved ends 26, 27 of the arms 23, 24 of section 20. The curved ends 26, 27 slide along or in proximity to the walls 91 during pivoting movement between the sections 20, 30.

The section portion 32 also includes a pair of spaced-apart arms 37, 38 that extend in a proximal direction. The arms 37, 38 include curved proximal ends that facilitate pivoting movement with the section 40. The inner surfaces of the arms 37, 38 that face towards the longitudinal centerline C may be substantially smooth to further facilitate pivoting movement with the section 40. Apertures 39 extend through each of the arms 37, 38 to form a portion of the axis 61. The proximal aperture 34 extends through the wall 91 and into the space between the arms 37, 38.

Third section 40 is positioned proximal to and adjacent to the second section 30. Section 40 includes a first surface 141 and an opposing second surface 142. Section 40 includes an axial length that extends from a distal end 41 that faces towards the section 30 and an opposing proximal end 42.

A receptacle 43 is completely contained within the interior of the section 40 and extends through the first and second surfaces 141, 142. The receptacle 43 includes a fixed shape that does not change during flexing of the implant 10. The receptacle 43 includes an inner surface that is interrupted by apertures 47, 48. Apertures 47 that form a portion of axis 61 and apertures 48 that form a portion of axis 62 may extend into the receptacle 43. Apertures 49 at the distal and proximal ends 41, 42 extend along the centerline C and open into the receptacle 43.

Section 40 also includes a pair of projections 44 that extend laterally outward away from the longitudinal centerline C. The projections 44 include a distal surface 45 that face towards the section 30. The distal surface 45 may be curved and substantially match the shape of the ends of the arms 37, 38. The projections 44 also include a proximal surface 46 that faces towards section 50. The proximal surface 46 may also include a curved shape that corresponds to the section 50.

Section 50 is positioned at the proximal section of the implant 10 and includes the proximal end 12. Section 50 includes a first surface 151 and an opposing second surface 152. Teeth may be positioned on one or both surfaces 151, 152 to maintain the position of the implant 10 in the intervertebral space. Section 50 includes a pair of spaced-apart arms 51, 52 that extend in a distal direction. The arms 51, 52 include curved distal ends 54, 55 that match the proximal surfaces 46 and facilitate pivoting movement with the section 40. The inner surfaces of the arms 51, 52 that face towards the longitudinal centerline C may be substantially smooth to further facilitate pivoting movement with the section 40. Apertures 53 extend through each of the arms 51, 52 to form a portion of the axis 62. A proximal wall may include an aperture 56 for connecting the implant 10 with an insertion instrument. The aperture 56 may be positioned along the longitudinal centerline C. The aperture 56 may be threaded to engage with corresponding threads on the insertion instrument.

An attachment member 70 may be sized to fit within the aperture 56. The attachment member 70 may include an enlarged flange 71 and an outwardly-extending shaft 72. The enlarged flange 71 may seat against the inner surface of the section 50 to prevent the attachment member 70 from pulling through the aperture 56 during attachment with an insertion instrument. The shaft 72 may be threaded to engage with corresponding threads on the aperture 56. An end of the shaft 72 facing away from the flange 71 may include a receiver to attach to an insertion instrument as explained below.

The pivot axes 60, 61, 62 are formed by one or more connectors 80. The connectors 80 include an elongated shape to extend through at least portions of two of the sections 20, 30, 40, 50. The connectors 80 are also sized to fit into the various apertures in the sections 20, 30, 40, 50 that are aligned along the pivot axes 60, 61, 62. Various types of connectors 80 may be used in the implant 10. Each of the connectors 80 within the implant 10 may be the same, or two or more different connectors 80 may be used within the implant 10.

As illustrated in FIG. 2, the connectors 80 may include an enlarged head 81 with an outwardly-extending shaft 82. The shaft 81 may include a larger first section adjacent to the head 81 and a smaller second section. The first section may be threaded to engage with corresponding threads in the aperture in which it is inserted. By way of example, the connectors 80 that form the first pivot axis 60 may be threaded onto apertures 25 in the first section 20. The connectors 80 also include ends 84 opposite from the heads 81. The various apertures on the sections that receive the heads may include a countersunk shape for the heads 81 to be recessed below the exterior lateral surfaces of the sections.

The sections 20, 30, 40, 50 are aligned in an end-to-end and overlapping arrangement for the various apertures to align along the respective pivot axes 60, 61, 62. The first and second sections 20, 30 overlap with the apertures 25 in the first section 20 being aligned with the corresponding apertures 36 in the second section 30. A first connector 80 extends through the aligned apertures 25, 36 on a first lateral side of the centerline C, and a second connector 80 extends through the aligned apertures 25, 36 on the opposing lateral side.

Likewise, the second and third sections 30, 40 overlap and the various apertures align along the pivot axis 61. The pivot axis 61 is formed by a first connector 80 that extends through apertures 39, 47 on a first lateral side of the centerline C, and a second connector 80 that extends through the corresponding apertures 39, 47 on a second lateral side of the centerline C.

The third and fourth sections 40, 50 overlap and the respective apertures align to form the pivot axis 62. A first connector 80 extends through apertures 48, 53 on a first lateral side of the centerline C, and a second connector 80 that extends through the corresponding apertures 48, 53 on a second lateral side of the centerline C. One or more of the pivot axes 60, 61, 62 may be perpendicular to the longitudinal centerline C. In one embodiment, the pivot axes 60, 61, 62 are parallel.

Figure 5:
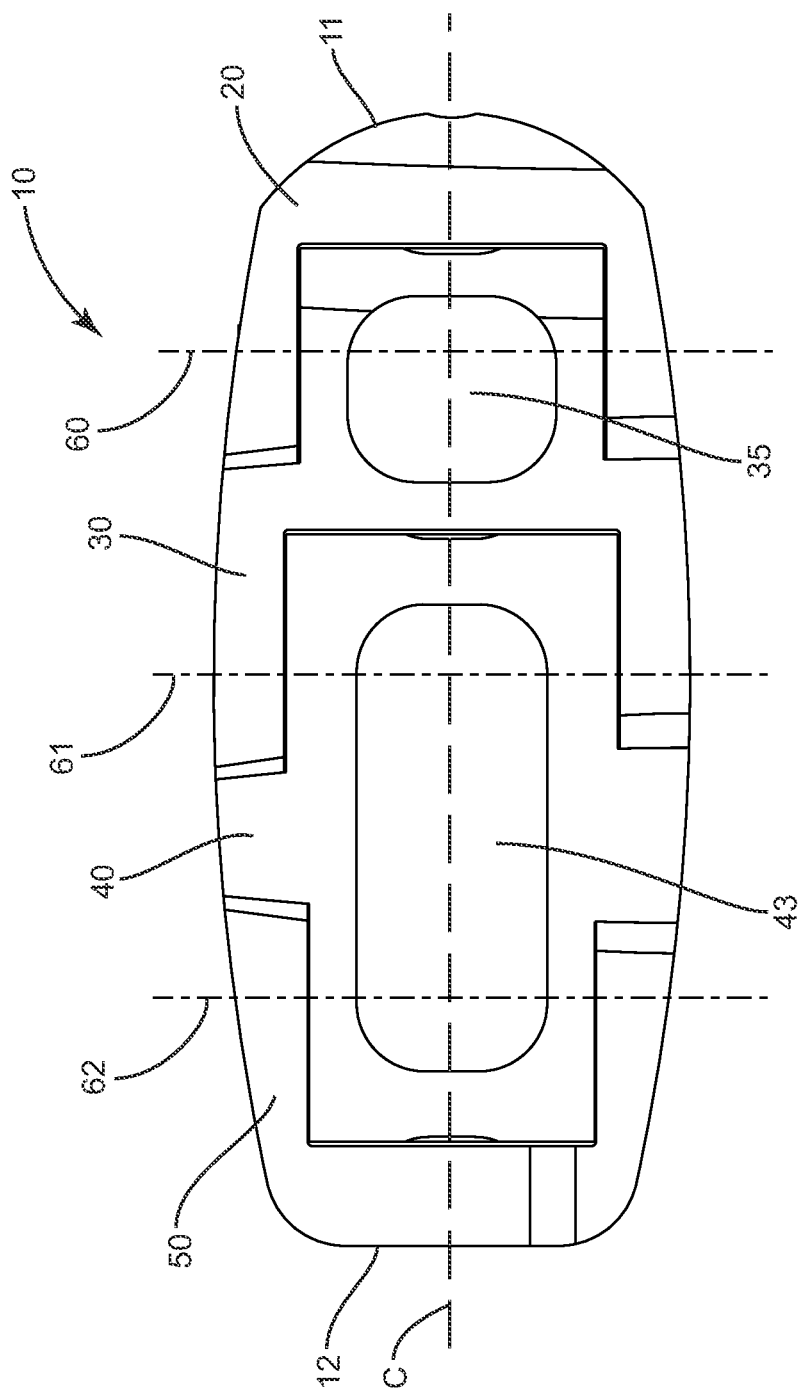
FIG. 5 is a top view of a flexible spinal implant.

FIG. 5 is a top view of an implant 10 illustrating the position of the pivot axes 60, 61, 62 relative to the sections 20, 30, 40, 50. The sections 20, 30, 40, 50 are arranged in an end-to-end orientation with the adjacent sections being in an overlapping orientation. The first section 20 overlaps with the second section 30 with the pivot axis 60 extending across the receptacle 35 in the second section 30. The second section 30 overlaps with the third section 40 with the pivot axis 61 extending across the receptacle 43 in the third section 40. Likewise, third section 40 overlaps with the fourth section 50 with the pivot axis 62 also extending across the receptacle 43.

Figure 6:
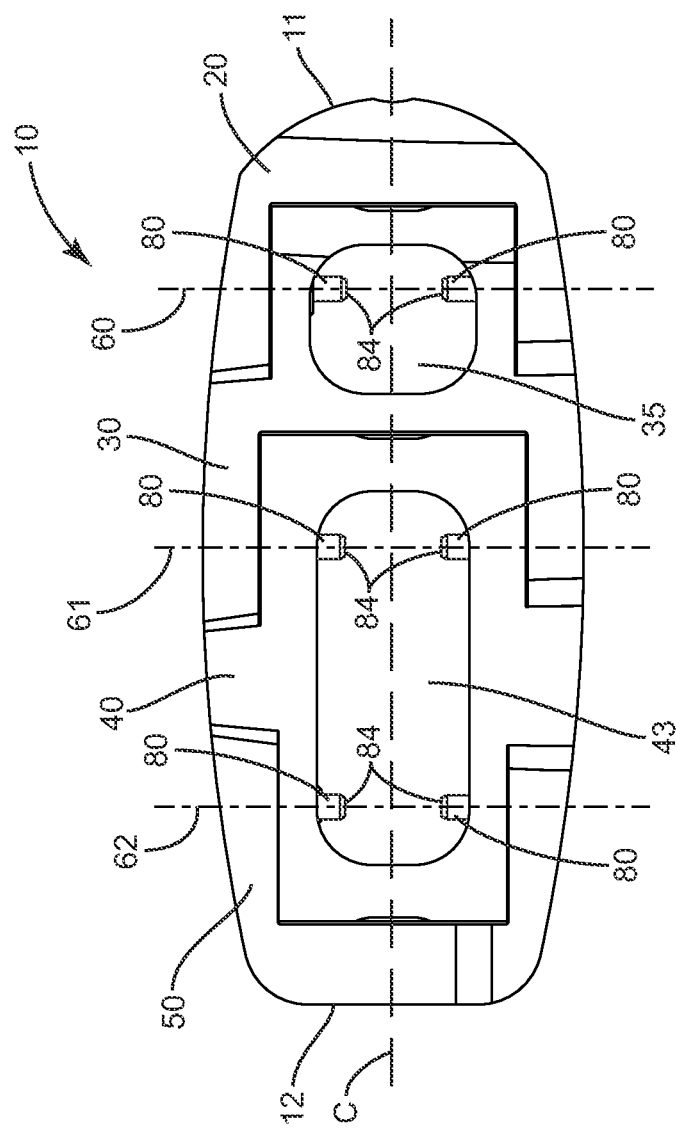
FIG. 6 is a top view of a flexible spinal implant.

The connectors 80 in FIG. 5 include a length to remain within the walls of the sections 20, 30, 40, 50 with the ends 84 positioned away from the receptacles 35, 43. The connectors 80 may further act as plugs to fill the apertures 36, 47, 48 in the walls of the sections 30, 40 and prevent the escape of bone growth material that is placed in the receptacles 35, 43. In one embodiment, the ends 84 are positioned flush with the walls of the receptacles 35, 43. FIG. 6 illustrates an embodiment with the connectors 80 having a greater length with the ends 84 extending into the receptacles 35, 43.

In the embodiments of FIGS. 5 and 6, the connectors 80 are spaced apart along the respective pivot axes 60, 61, 62. A gap is formed between the ends 84 of the connectors 80. The gap is positioned in the respective receptacle 35, 43.

Figure 7:
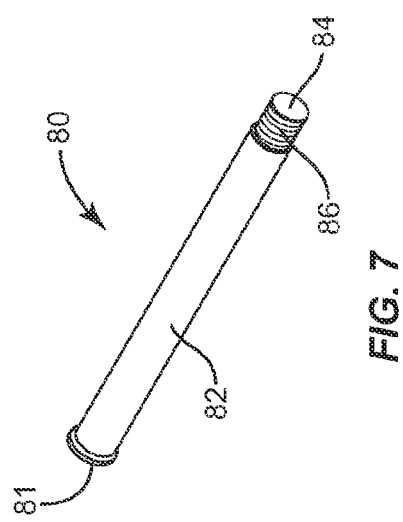
FIG. 7 is a perspective view of a connector with an enlarged length.

FIG. 7 illustrates another connector 80 for use with the implant 10. The connector 80 includes an enlarged length measured between the head 81 and end 84. The length of the connector 80 provides for a single connector to form the respective pivot axis 60, 61, 62. The length also provides for the connector 80 to extend across the respective receptacle 35, 43. Threads 86 may be located at or in proximity to the end 84 to engage with threads on the corresponding aperture in one of the sections. By way of example, if connector 80 is used for forming the pivot axis 60, the head 81 is positioned at the aperture 25 with the threads 86 engaging with an opposing threaded aperture on the other side of the receptacle 35. The length may also position the end 84 laterally outward beyond the laterally sides of the section 20 with a separate fastener (e.g., nut, washer, lock cap) fitted on the threads 86 to maintain the attachment.

Figure 8:
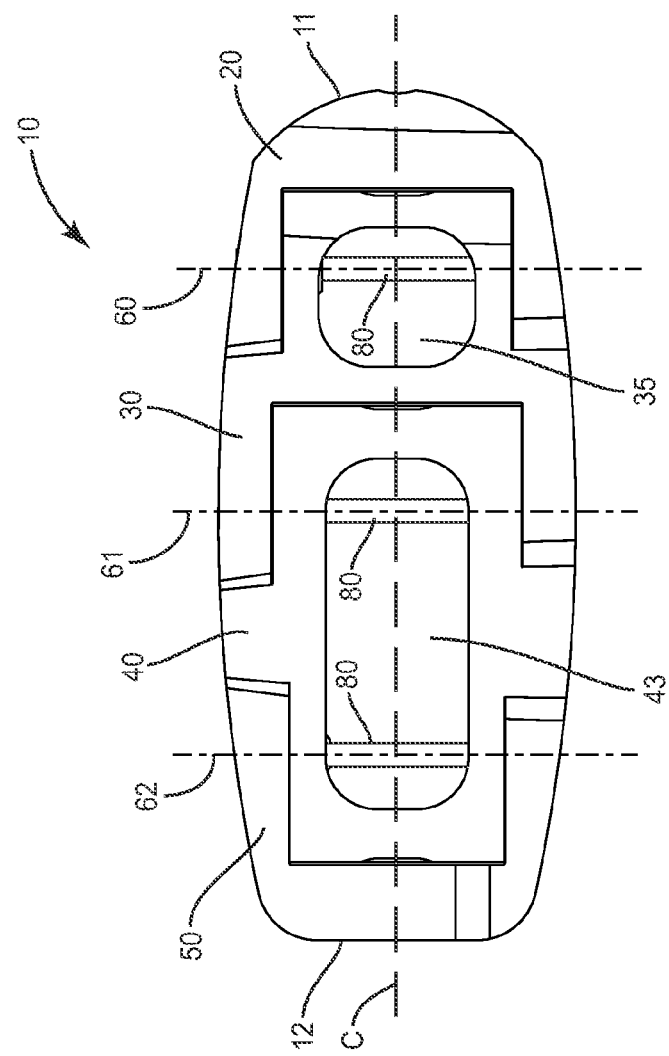
FIG. 8 is a top view of a flexible spinal implant.

FIG. 8 illustrates a top view of an implant 10 with the elongated connectors 80. The connectors 80 extend across the receptacles 35, 43.

The pivot axes 60, 61, 62 may extend along a plane that cuts through the sections 20, 30, 40, 50 between the superior surface 16 and the inferior surface 17. The receptacles 35, 43 are transverse to and extend through the plane.

The implant 10 may be configured for the sections 20, 30, 40, 50 to pivot in the two opposing directions away from the plane. This allows for the sections 20, 30, 40, 50 to pivot upward in a first direction (as illustrated in FIG. 3), and also downward in an opposing second direction. One or more of the sections 20, 30, 40, 50 may also be configured to prevent pivoting movement in one of the two directions. This selective pivoting may be caused by the shape of the apertures and connectors 80 that form the pivot axes 60, 61, 62. The selective pivoting may also be caused by the shape of the sections 20, 30, 40, 50. By way of example, lateral surfaces 91 of the second section 30 may be shaped to contact against the inferior surface 133 of the arms 23, 24 and prevent movement in the second, downward direction. One or more the sections 20, 30, 40, 50 may also be configured to limit the amount of movement in one or both directions.

Figure 9:
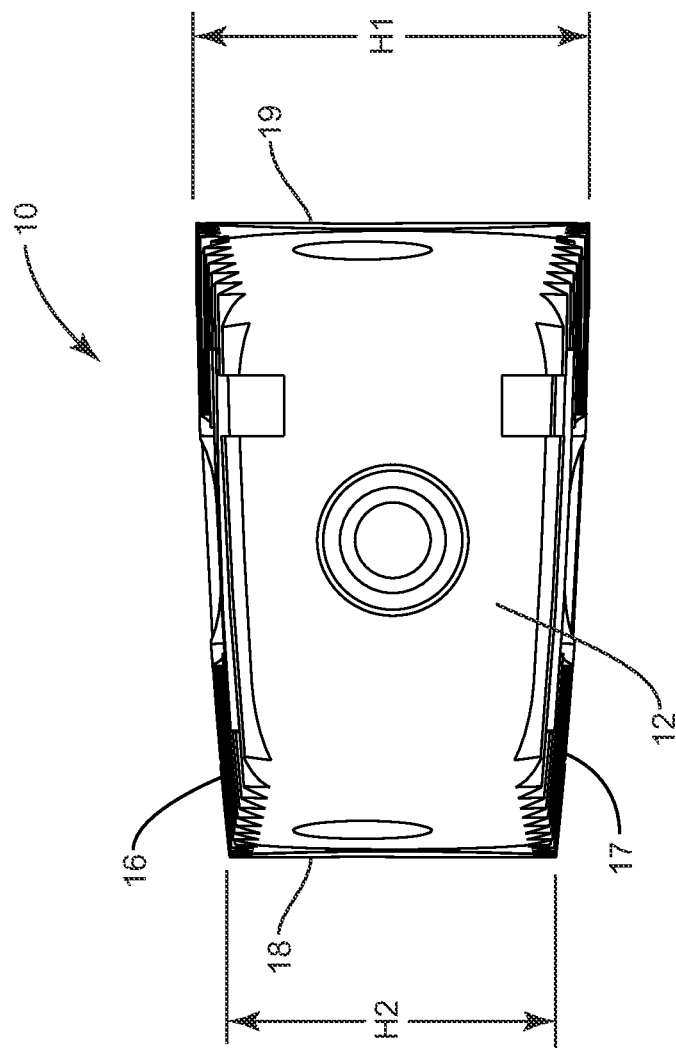
FIG. 9 is a rear view of a flexible spinal implant.

FIG. 9 includes a rear view of an implant 10. The height H1 of the lateral side 19 measured between the superior and inferior sides 16, 17 is greater than the height H2 of the opposing lateral side 18. The superior and inferior sides 16, 17 form an angle to accommodate the curvature of the spine and/or the shape of the intervertebral space. In one embodiment, the superior and inferior sides 16, 17 form an angle of about 6°. Other embodiments may include the lateral side 19 with a smaller height than the opposing lateral side 18. Alternatively, the heights H1, H2 may be substantially the same.

One or both of the superior and inferior sides 16, 17 may include a convex curve. The curve may include a radius in the range of between about 200-350 mm.

As illustrated in FIG. 4, the height measured between the superior and inferior sides 16, 17 may be the largest towards the longitudinal center of the implant 10. In this embodiment, sections 30 and 40 include greater heights than sections 20 and 50.

Figure 10:
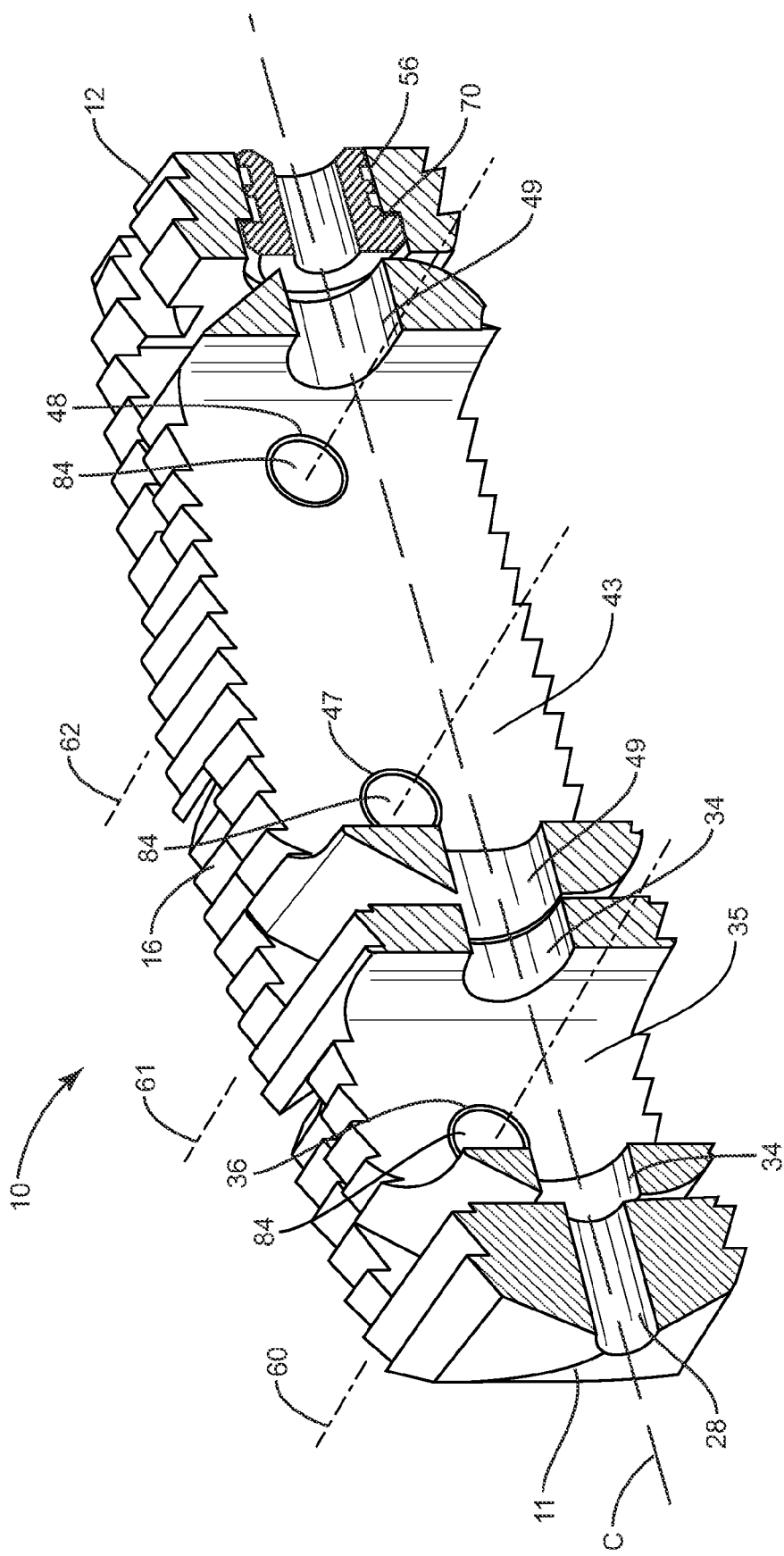
FIG. 10 is a sectional view of the flexible spinal implant of FIG. 1 cut along line X-X.

FIG. 10 is a longitudinal sectional view of the implant 10. A central longitudinal opening extends through the length of the implant 10. The opening is formed by apertures 28, 34, 49, 56 in the respective sections 20, 30, 40, 50. The central opening aligns along the longitudinal centerline C when the implant 10 is in the straight configuration as illustrated in FIG. 10.

The implants may include various numbers of sections. The embodiments described in FIGS. 1-10 each include four sections 20, 30, 40, 50 that are attached together along three pivot axes 60, 61, 62. FIGS. 11 and 12 illustrate an implant 200 with three sections 220, 230, 240 attached together along two pivot axes 260, 261. The pivot axes 260, 261 are designed to give flexibility to the implant 200. Sections 220, 230 are pivotally attached together by a first pair of connectors 280 at pivot axis 260, and sections 230, 240 are pivotally attached together by a second pair of connectors 280 at pivot axis 261.

The implant 200 also includes a first receptacle 231 in section 230, and a second receptacle 241 in section 240. In this embodiment, pivot axis 260 extends across receptacle 231, and pivot axis 261 extends across receptacle 241.

Figure 13:
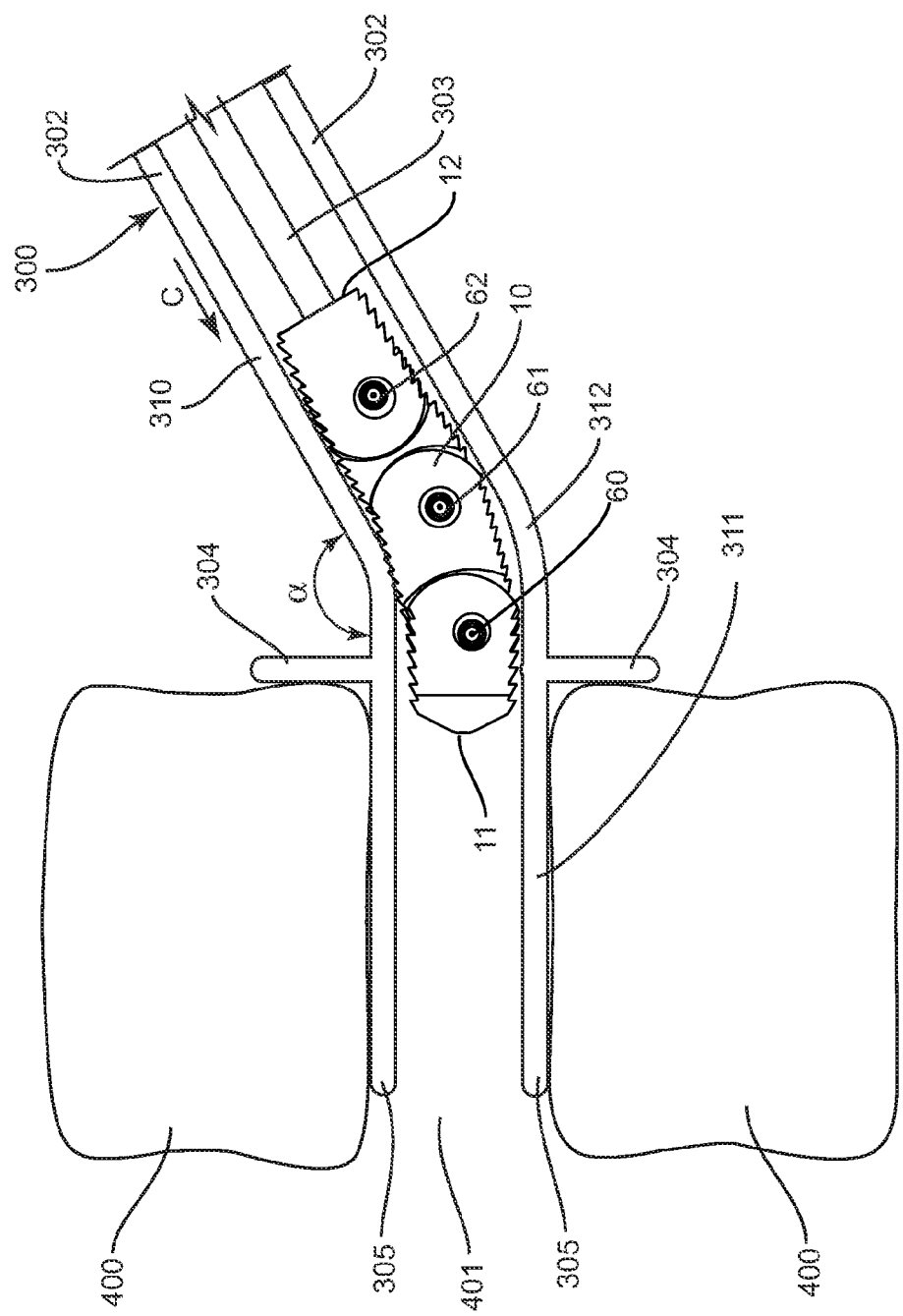
FIG. 13 is a side view of an implant in an insertion tool.

FIG. 13 illustrates an implant 10 being inserted into a patient. The implant 10 is sized to be inserted into the intervertebral space 401 between the vertebral members 400. An insertion tool 300 is used for placing the implant 10 in the space 401. The insertion tool 300 includes a pair of spaced-apart arms 302. The arms 302 include a proximal section 310 and a distal section 311 that are each substantially straight. The sections 310, 311 are connected at an elbow 312 that forms an angle α. In some embodiments, the angle α may vary between a range of between about 120° to about 165°. The arms 302 may include rails or other structure to engage with the implant 10 and also allow the implant 10 to move longitudinally along the arms 302.

Stops 304 extend outward away from a centerline formed between the arms 302. The stops 304 control the amount of insertion of the distal section 311 into the intervertebral space 401. FIG. 13 illustrates the insertion tool 300 fully inserted into the intervertebral space 401 with the stops 304 contacting against the vertebral members 400 and distal ends 305 of the arms 302 being positioned in the intervertebral space 401.

A pushing member 303 is positioned between the arms 302. The pushing member 303 is movable along the longitudinal length of at least the proximal section 310 of the arms 302 to move the implant 10 into the intervertebral space 401. The pushing member 303 includes a distal end that engages with the attachment member 70 mounted in the implant 10.

In use, the insertion tool 300 is positioned relative to the vertebral members 400 and the intervertebral space 401. The implant 10 may be mounted in the tool 300 during the alignment process, or may be mounted in the tool 300 after alignment. In either event, bone growth material may be placed in one or both receptacles 35, 43.

The implant 10 is moved along the length of the proximal section 310 by a force that is applied through the pushing member 303. The sections of the implant 10 may be aligned in a straight orientation when the implant is the proximal section 310 (i.e., the sections are in-line which is defined as having an angle of 0° at each of the pivot axes 60, 61, 62). As the implant 10 moves through the elbow 312, the implant 10 pivots at the pivot axes 60, 61, 62. In some embodiments, the implant 10 is able to pivot up to about 90° at each of the pivot axes 60, 61, 62. This flexibility allows for the implant 10 to move beyond the elbow 312 and to the distal section 311. Because the receptacles 35, 43 are contained with one of the sections, their shapes and sizes do not change during pivoting motion of the implant 10. This maintains the bone growth material in the receptacles 35, 43.

Figure 14:
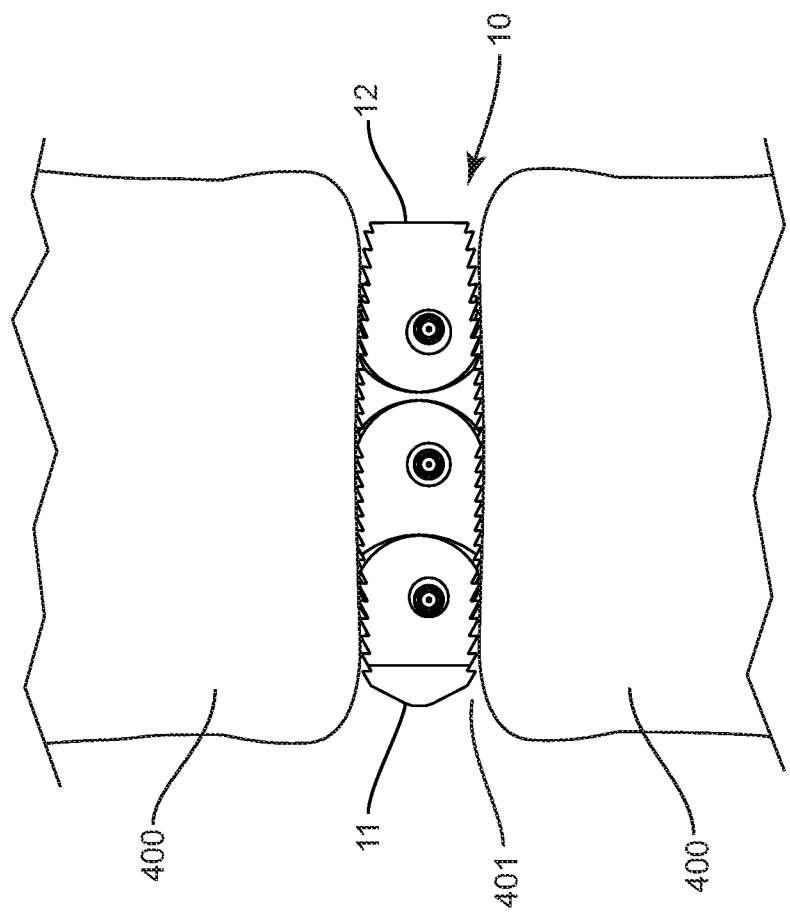
FIG. 14 is a side view of an implant positioned in an intervertebral space between vertebral members.

Once the implant 10 is positioned in the intervertebral space 401, the insertion tool 300 is removed. This includes detaching the pushing member 303 from the implant 10, and removing the tool 300 from the patient. As illustrated in FIG. 14, the implant 10 is flexible to conform to the shape of the space 401 and to contact against the vertebral members 400.

The implant 10 may be flexible in two opposing directions. FIG. 13 illustrates an implant 10 flexing in a first direction. The amount of flexibility in the second direction may be the same or less than the amount in the first direction. In one embodiment, the amount of flexibility in the first direction is about 90° from the in-line orientation (defined as an angle of +90°) and the amount of flexibility in the second direction is about 5° from the in-line orientation (defined as an angle of −5°). Further, the amount of flexibility may be the same or different at the various pivot axes along the length of the implant. By way of example, the amount of flexibility at the pivot axis 60 may be greater than the amount at pivot axis 62.

The implant 10 may be inserted into the patient with a variety of different approaches such as with a DLIF approach and with an ALIF approach. Various other approaches may also be employed with the implant 10. The flexibility of the implant 10 accommodates the various approaches and movement around the anatomical features such as the iliac crest and the ribs. The implant 10 may be used along various locations along the spine including the thoracic, lumbar, and sacrolumbar regions.

Other embodiments of flexible spinal implants and insertion of the flexible implants into a patient are disclosed in U.S. patent application Ser. Nos. 12/533,877 and 12/605,415 which are assigned to the same entity as the present application. These two applications are herein incorporated by reference in their entireties.

Figure 15:
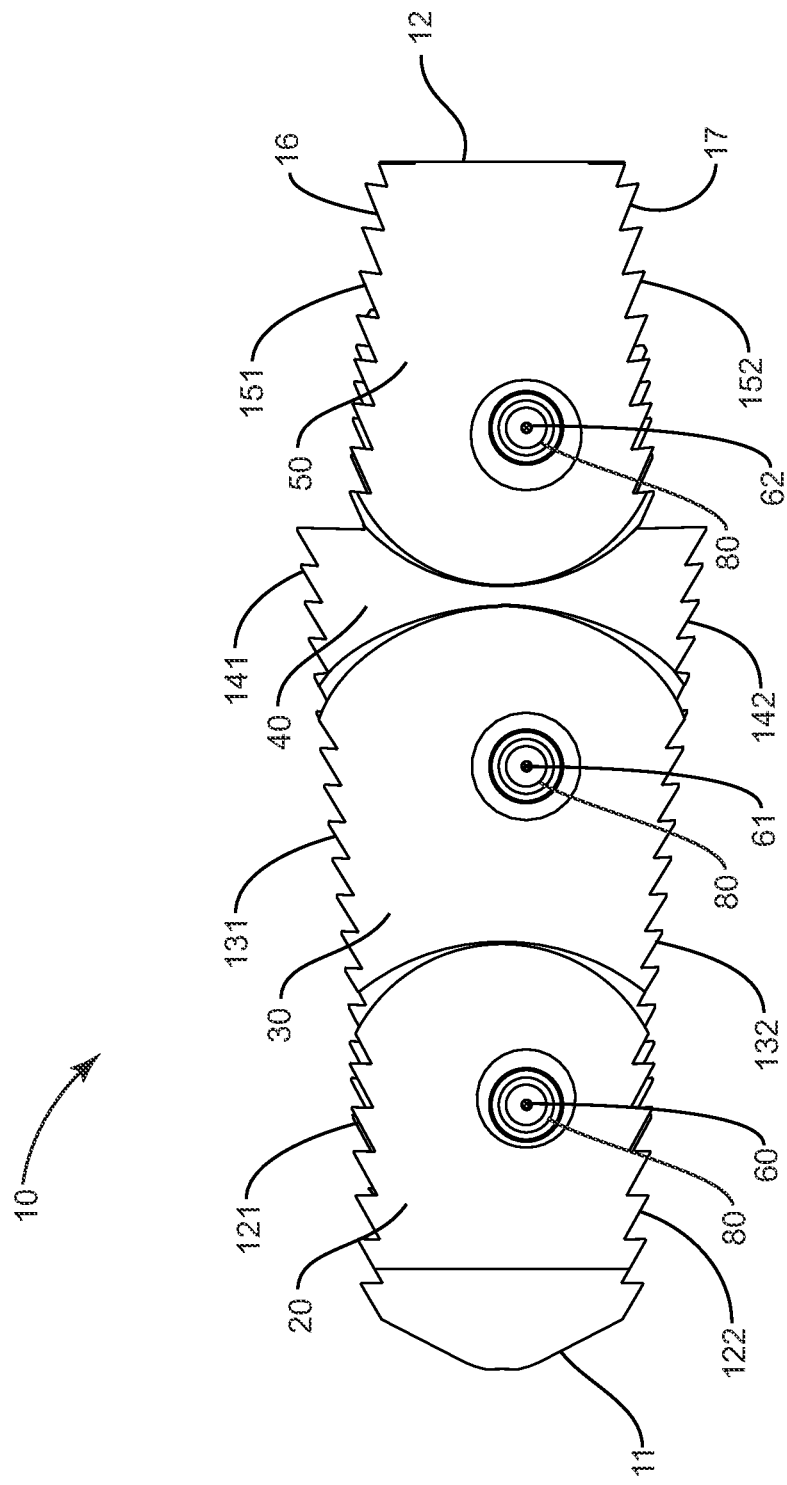
FIG. 15 is a side view of the flexible spinal implant.

FIG. 4 includes the sections 20, 30, 40, 50 with heights measured between opposing superior and inferior surfaces 121 and 122, 131 and 132, 141 and 142, 151 and 152 that substantially match the adjacent sections. This gives the implant 10 overall continuous superior and inferior sides. The implant 10 may also include one or more sections with different heights such that one or both of the inferior and superior sides are not continuous. FIG. 15 includes sections 40 with a different height than adjacent section 50. In this embodiment, both the overall superior and inferior sides of the implant are not continuous at the junction between sections 40 and 50. Other embodiments may include just a single side (i.e., inferior or superior) of the implant 10 not being continuous. Other embodiments include two or more sections having different heights than adjacent sections to cause discontinuities in the overall inferior and superior sides.

Figure 16:
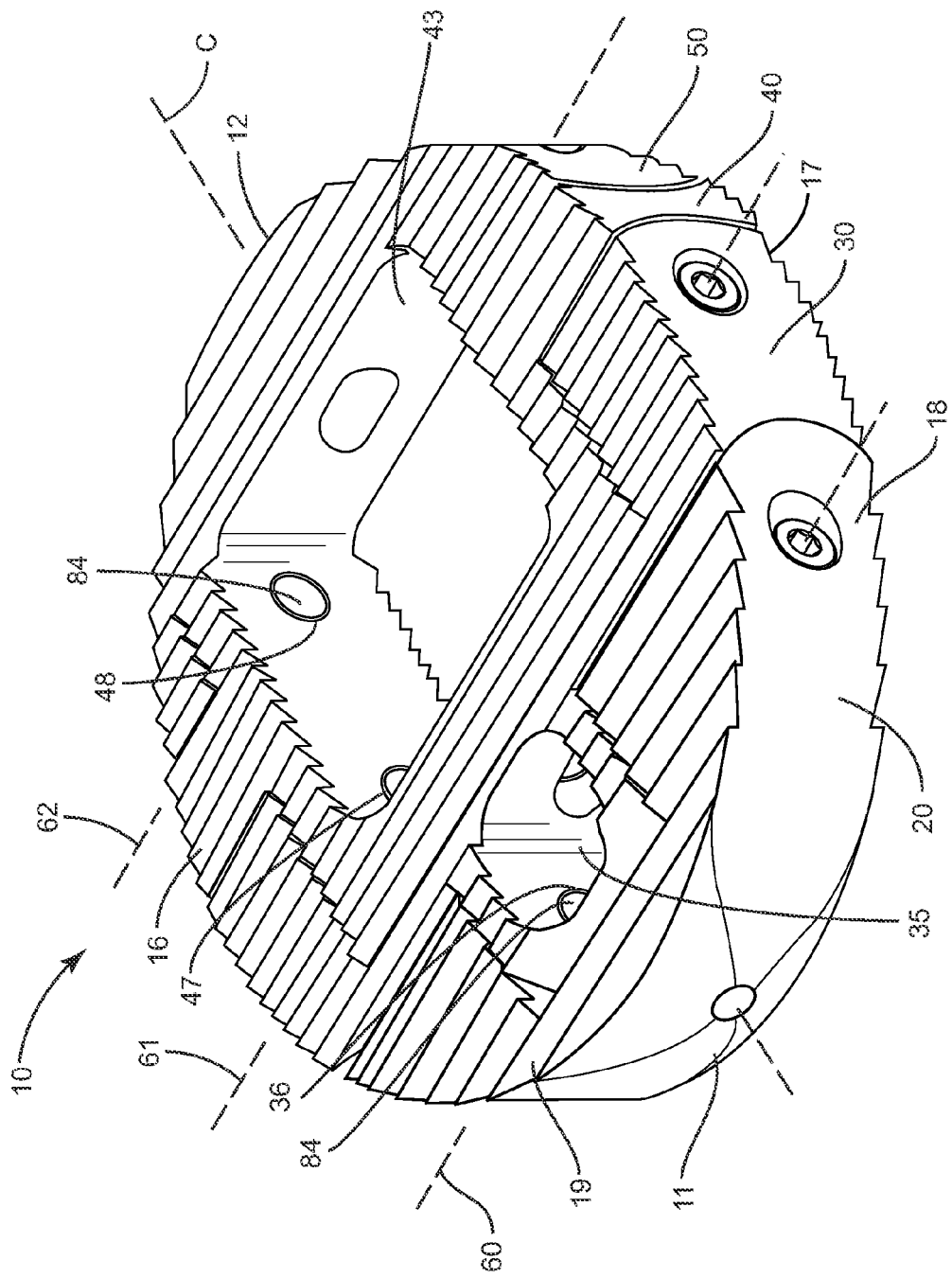
FIG. 16 a perspective view of a flexible spinal implant in a straight orientation.

The implant 10 may have different shapes depending upon the application. FIG. 1 includes an implant 10 having a substantially rectangular shape when viewed from the top and bottom. FIG. 16 includes an implant 10 with a circular shape when viewed from the top and bottom.

The various implants and insertion tools may be used during surgical procedures on living patients. These may also be used in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A spinal implant comprising:
a plurality of monolithically formed sections each having a distal end and a proximal end, each of the sections also having a superior side and an opposing inferior side, a first one of the sections including a receptacle bounded within an interior of the first section and having a fixed size and shape, the receptacle being open on the superior and inferior sides;
a plurality of hinges that pivotally join together the sections in an end-to-end and articulating arrangement, each of the plurality of hinges connecting together two of the plurality of sections, the plurality of hinges being aligned along a plane;
the receptacle being aligned transverse to and extending across the plane, the receptacle being open in both directions that face away from the plane,
wherein a second one of the hinges that connects the first one of the sections and a third one of the sections extends across the receptacle, the first and second hinges being spaced apart within the receptacle.

2. The implant of claim 1, wherein a longitudinal centerline extends through the distal and proximal ends of each section, across each of the plurality of hinges, and through the receptacle.

3. The implant of claim 1, wherein a first one of the hinges that connects the first one of the sections and a second one of the sections extends across the receptacle.

4. The implant of claim 1, wherein at least one of the plurality of hinges includes first and second connectors that are spaced apart by a gap.

5. The implant of claim 1, wherein a second one of the sections includes another receptacle that is bounded within an interior of the second section and has a fixed size and shape with the receptacle being open on the superior and inferior sides.

6. The implant of claim 5, wherein the receptacles in the first and second sections have different sizes.

7. The implant of claim 1, wherein at least one of the plurality of hinges includes a single connector.

8. A spinal implant comprising:
a plurality of sections pivotally attached together and aligned in an end-to-end orientation with each having a superior side and an inferior side;
a first one of the sections including a receptacle contained within an interior of the first section and having distal, proximal, and lateral side walls, the receptacle being open on the superior and inferior sides and having a fixed size and shape;
the first section and a second one of the sections being pivotally connected at a pivot axis that extends across the receptacle, the pivot axis including a first connector that extends through first portions of the first and second sections and a second connector that extends through second portions of the first and second sections;
the first and second connectors being spaced apart along the pivot axis by a gap that is located in the receptacle.

9. The implant of claim 8, wherein the first and second connectors extend through the lateral side walls and into the receptacle.

10. The implant of claim 8, wherein the first and second sections include a first pair of apertures that are aligned along the pivot axis and receive the first connector, and a second pair of apertures that are aligned along the pivot axis and receive the second connector.

11. The implant of claim 8, wherein the pivot axis extends between the superior and inferior sides of the first section.

12. The implant of claim 8, wherein the plurality of sections includes a third section that is attached to an opposing side of the first section from the second section, the third section being pivotally attached to the first section at another pivot axis that also extends across the receptacle.

13. The implant of claim 12, wherein the pivot axes are parallel and spaced apart along the receptacle.

14. The implant of claim 8, wherein the second section includes a pair of spaced apart flanges that overlap with the first section, the pivot axis extending through the flanges.

15. The implant of claim 8, further comprising a longitudinal opening that extends along a longitudinal length of the plurality of sections, the longitudinal opening formed by at least one aperture in each of the plurality of sections, the longitudinal opening being centered about a longitudinal centerline of the implant.

16. The implant of claim 8, wherein the plurality of sections are monolithically formed.

17. A spinal implant comprising:
first and second monolithically formed sections each having a distal end and a proximal end, lateral sides that extend between the ends, and a superior side and an inferior side;
a receptacle contained within an interior of the first section and having a fixed size and shape, the receptacle having a continuous side wall and being open on the superior and inferior sides;
a hinge that extends through the lateral sides of each of the first and second sections between the distal and proximal ends of each section, the hinge pivotally connects the first and second sections along a pivot axis, the hinge positioning the sections together in an end-to-end configuration with a longitudinal axis extending through the distal and proximal ends of each of the sections and between the superior and inferior sides and between the lateral sides;
the pivot axis extending across the receptacle and across the longitudinal axis.

18. The implant of claim 17, wherein the hinge includes a pair of connectors that include a head positioned at the lateral sides of the sections and an end, the ends of the pair of connectors being spaced apart along the pivot axis by a gap.

19. The implant of claim 18, wherein the ends of the connectors are positioned in the receptacle.

20. The implant of claim 18, wherein the ends of the pair of connectors are positioned in one of the first and second sections and are spaced away from the receptacle.

\* \* \* \* \*